United States Patent [19]

Ali

[11] Patent Number: 4,583,526
[45] Date of Patent: Apr. 22, 1986

[54] FLEXIBLE ENDOSCOPE STRUCTURE

[76] Inventor: Mir A. Ali, 26430 Via Marquette, Lomita, Calif. 90717

[21] Appl. No.: 691,510

[22] Filed: Jan. 14, 1985

[51] Int. Cl.⁴ ............................................. A61B 1/06
[52] U.S. Cl. ................................. 128/6; 128/303.1; 128/395
[58] Field of Search ............... 128/4, 6, 7, 8, 9, 303.1, 128/395

[56] References Cited

U.S. PATENT DOCUMENTS

| | | | |
|---|---|---|---|
| 3,858,577 | 1/1975 | Bass et al. | 128/8 |
| 3,906,953 | 9/1975 | Wallace et al. | 128/303.1 |
| 4,170,997 | 10/1979 | Pinnow et al. | 128/4 X |
| 4,289,378 | 9/1981 | Remy et al. | 128/303.1 X |
| 4,408,602 | 10/1983 | Nakajima | 128/395 X |
| 4,419,987 | 12/1983 | Ogiu | 128/4 |
| 4,458,683 | 7/1984 | Saito et al. | 128/395 |

Primary Examiner—William H. Grieb
Attorney, Agent, or Firm—William C. Babcock

[57] ABSTRACT

A flexible endoscope with a carbon dioxide laser connected thereto for simultaneous viewing and performance of a surgical operation on either exterior or interior tissue of a patient. The laser operates at 10.6 microns, with the laser beam being transmitted through a flexible bundle of drawn fiber optics that are held in adjacently disposed fixed relationship by a flexible sheath. Each laser beam transmitting fiber optic has a core of infra red transmitting true amorphous chalcogenide glass that is clad by a thin flexible film of material having a lesser refractive index. The infra red transmitting glass will preferably have a transmission efficiency of between 38 to 62 percent.

6 Claims, 6 Drawing Figures

FLEXIBLE ENDOSCOPE STRUCTURE

DESCRIPTION OF THE PRIOR ART

In recent years it has become increasingly common in the medical profession to perform certain operations by the use of a laser beam, with an endoscope being used to permit the surgeon to view the affected area of the patient on which the laser beam will be directed.

Tissue is removed by vaporization in laser beam surgery. Such laser beam surgery occurs due to the tissue site of the patient on which the laser beam is directed absorbing the radiation that is subsequently transformed into heat energy to cause vaporization of the tissue and water that it contains. Heat from the tissue site tends to flow therefrom by thermal conductivity to cooler areas of the patient adjacent thereto. As such, tissue not exposed directly to the laser beam and not vaporized may suffer thermal shock.

To carry out laser surgery the surgeon must have at his disposal an endoscope coupled with a source of laser light of sufficient power to achieve rapid evaporation of the tissue site, with a minimum of thermal damage to the tissue portions adjacent thereto, and the endoscope having a sufficiently flexible structure that the laser beam emanating therefrom may be easily maneuvered inside a patient to be accurately directed onto the affected tissue site.

Prior art devices used in laser surgery have not met the above described criteria. An argon laser beam that emits energy around 0.5 microns will travel through a flexible fiber optic fiber, but its absorbion by tissue of a patient is dependent on the tissue color, and is accordingly not satisfactory for general surgery.

A neodymium-YAG laser beam at 1.06 micron may be directed through a flexible fiber optic, but it is difficult to vaporize tissue at the tissue site and control the damaged area.

A carbon dioxide laser beam at 10.6 microns quickly vaporizes tissue at a tissue site with minimum thermal shock to healthy tissue adjacent thereto. Various attempts have been made to utilize such a laser in laser surgery. The Pennow et al U.S. Pat. No. 4,170,997 discloses an instrument utilizing such a beam, but the material defining the fiber optic fiber is toxic as well as rigid, and the instrument is unsatisfactory for surgical use.

The difficulty of using a carbon dioxide laser beam for surgical purposes is summarized in lines 22-25, column 4 of the Bass et al U.S. Pat. No. 3,858,577 that issued Jan. 7, 1975 that states "This light, in the infra red, cannot be transmitted by any known flexible fiber optic delivery system because there is no materials with which to make a 10.6 micron transmitting fiber."

An endoscopic surgical laser system is disclosed in U.S. Pat. No. 3,906,953 that directs a laser beam at 10.6 micron from a carbon dioxide laser through a rigid metal tube to a desired site in a patients body. This system requires an incision for effective use in the human stomach.

The major object of the present invention is to provide an endoscope having a carbon dioxide laser associated therewith that operates at 10.6 microns, and with the endoscope including flexible fiber optic means that are flexible and operates effeciently to transmit infra red radiation and permit the latter to be directed as a beam onto a tissue site with minimum thermal damage being done to healthy tissue adjacent thereto.

SUMMARY OF THE INVENTION

A conveniontal present day endoscope that includes an elongate rigid body that supports an eye piece and is used in conjunction with a carbon dioxide laser that produces a beam at 10.6 microns.

The endoscope includes first, second and third flexible non-toxic fiber optics that extend as a bundle from a first end thereof, with the first fiber optic coupled to a source of light for illuminating a tissue site on which a surgeon desires to form a surgical operation. The second fiber optic is optically coupled to the eye piece to permit the surgeon to view the illuminated tissue site.

The third fiber optic is defined by an elongate flexible core of drawn amorphous chalcogenide glass that is greater than 10.6 microns in diameter and is clad in a glass having a lesser index of refraction. The third fiber optic is coupled to receive infra red radiation from the carbon dioxide laser, which radiation may be directed by a surgeon onto the illuminated tissue site by manipulation of the flexible bundle. The first, second and third fiber optics are preferably held in the form of a bundle by a heat shrinkable sheath of plastic that extends there around.

DESCRIPTION OF THE PREFERRED EMBODIMENT

Figure 1:
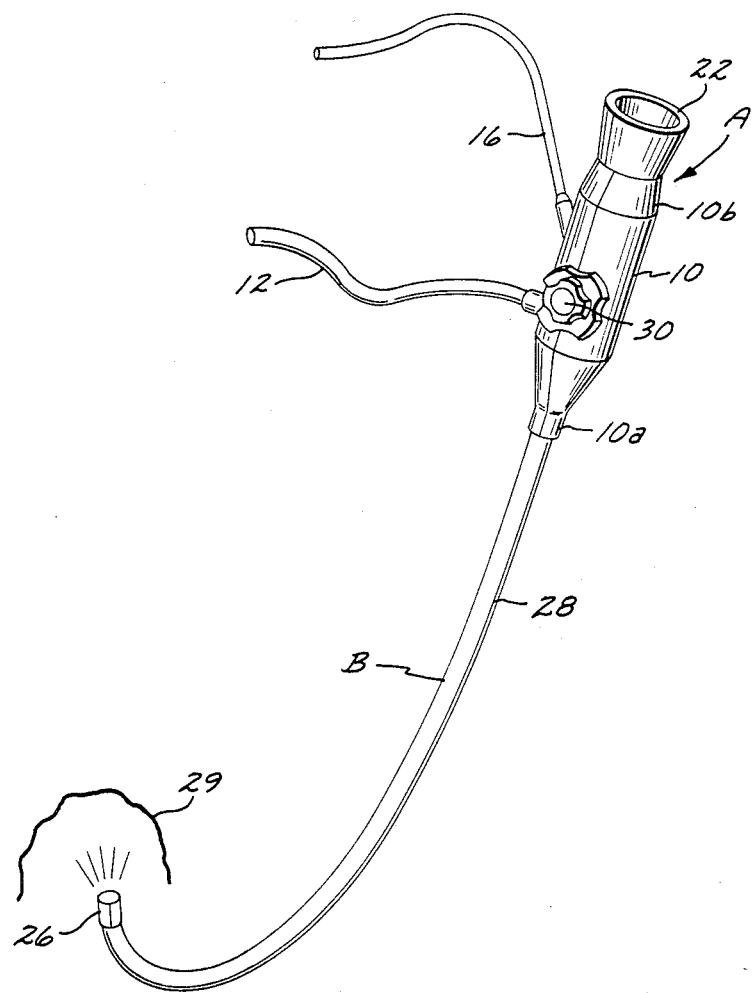
FIG. 1 is a side elevational view of a conventional present day endoscope.
Figure 2:
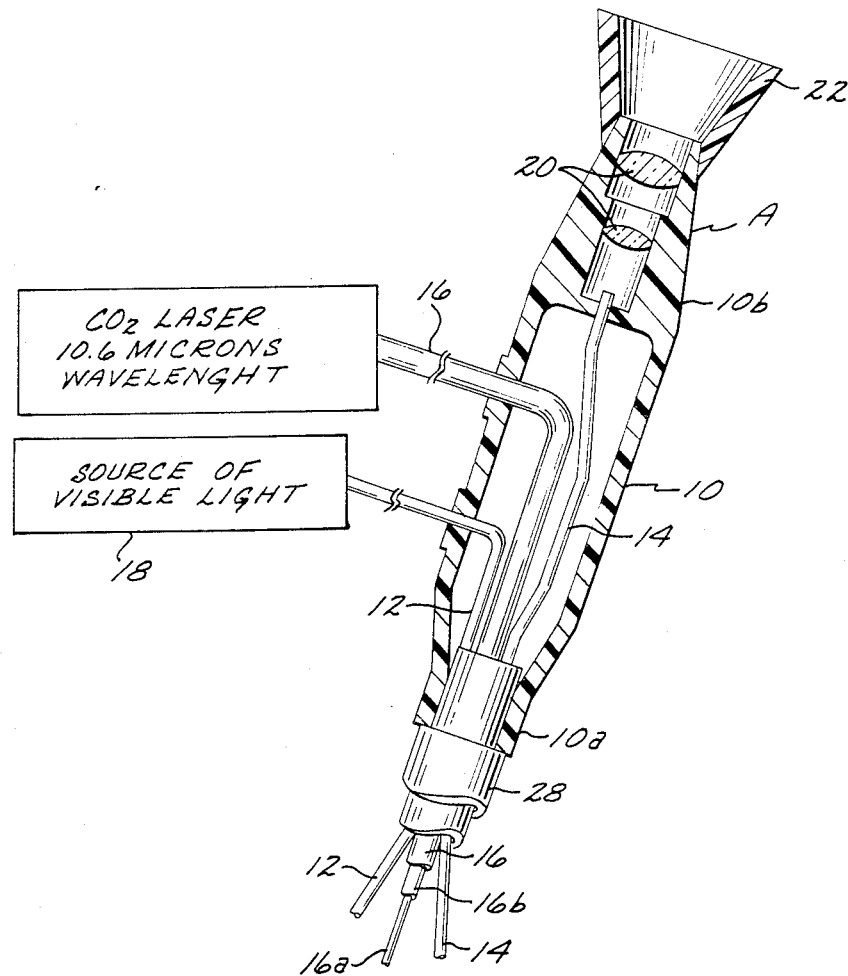
FIG. 2 is a longitudinal cross sectional view of the endoscope operatively associated with a source of visible light and a source of infra red radiation.

In FIG. 1 a conventional present day endoscope A is shown such as made by the Olympus Company, Japan, and the ACMI Corporation of New York, N.Y. In FIG. 2 it will be seen that the endoscope A includes an elongate rigid body 10 capable of being held by the hand (not shown) of a surgeon, which body includes a first end 10a and second end 10b.

First, second and third elongate fiber optics 12, 14 and 16 respectively which extend in side by side relationship from the first end 10a of body 10. The first fiber optic 12 extends from a side of body 10 to a source of visible light 18. The second fiber optic 14 terminates within the body 10 and by lens 20 is coupled to an eye piece 22 supported on the second end 10b of body 10.

The third fiber optic 16 extends outwardly from a side by the body 10 to a carbon dioxide laser 24 that emits a beam of infra red radiation at a wave length of 10.6 microns.

Figure 3:
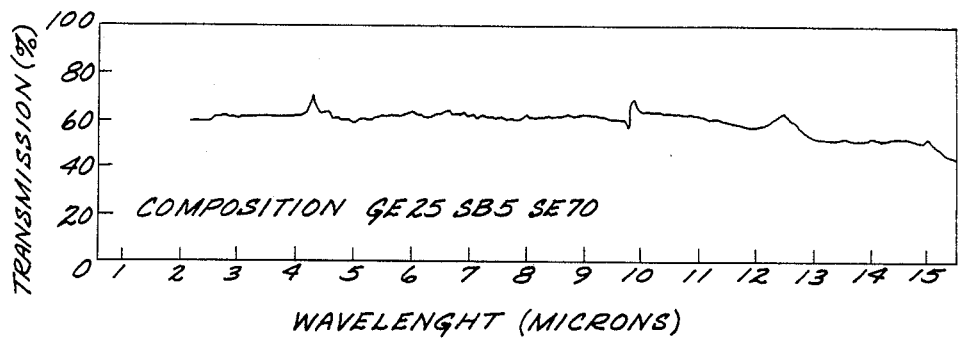
FIGS. 3 to 6 are infra red transmission charts for chalcogenide glasses of different compositions.
Figure 4:
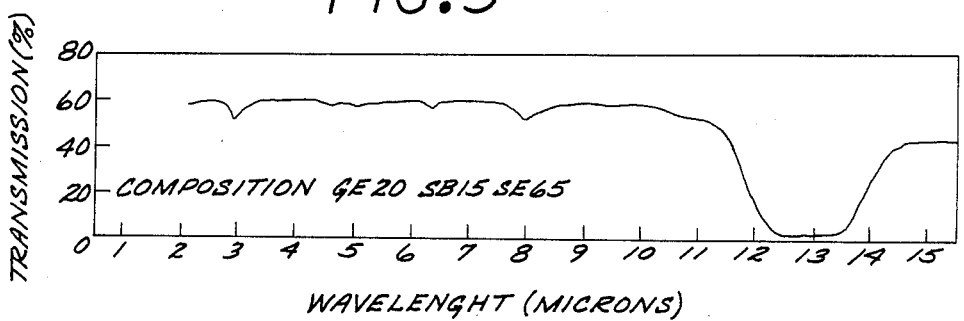
Figure 5:
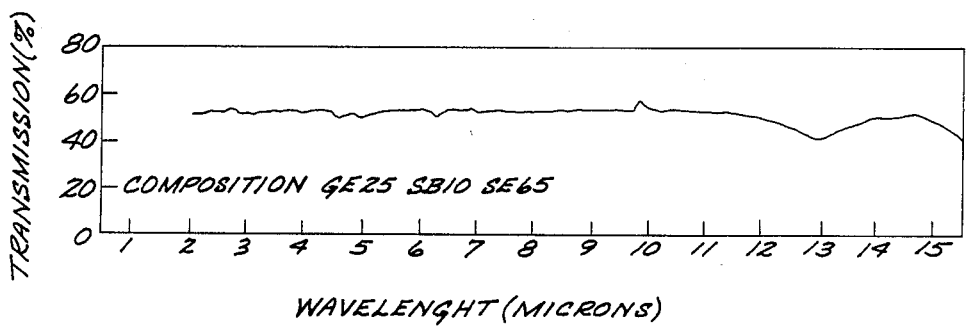
Figure 6:
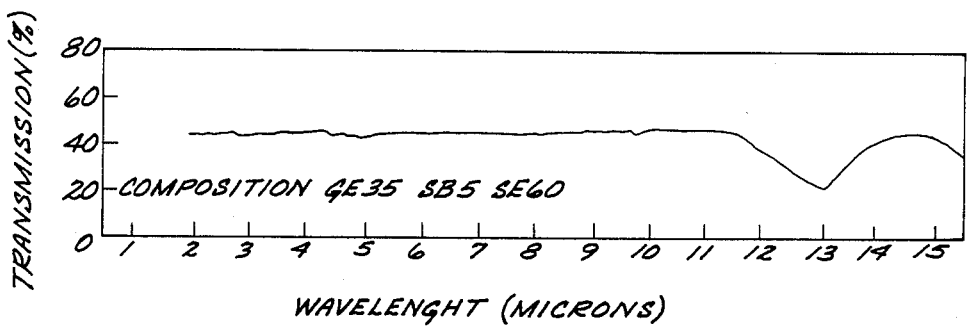

The third fiber optic 16 comprises a flexible core 16a of a drawn amorphous chalcogenide glass defined by germanium, antimony and selenium within the proportions shown in FIGS. 3 to 6 inclusive. The core 16a is surrounded by a cladding 16b of glass of a less refractive index that is fused thereto. The glass $Ge_{25} Sb_5 Se_{70}$ having the infra red transmission characteristics shown in FIG. 3 is preferred for forming the core 16a. Glass of this composition is non-toxic when brought in contact with a patient. The core 16a has a diameter greater than 10.6 microns of the infra red radiation.

The first, second and third fiber optics 12, 14 and 16 are held together as an elongate flexible bundle B by a heat shrinkable plastic sheath 28 shown in FIG. 2 that envelops the fiber optics. The bundle B terminates on the free end thereof in a cylindrical end piece 26 that may be disposed adjacent the tissue site 29 of a patient (not shown) that is to be treated surgically. The body 10 includes a manually operated control 30 that regulates the discharge of infra red radiation from the laser 24 to the bundle B.

In use the flexible bundle B is manipulated to dispose the end piece 26 adjacent the tissue site 29 which is illuminated by visible light from the first fiber optic 12, and the illuminated area by reflected light being visible to the surgeon (not shown) through the eye piece 22.

When the end piece 26 is so disposed, the control 30 may be used to discharge infra red radiation thereon at a wave length of 10.6 microns to achieve the beneficial results previously described. The third fiber optic 16 is preferably enclosed in a protective covering (not shown). The fabrication and processing of chalcogenide glasses from the Ge-Sb-Se system is described in U.S. National Aeronautics and Space Administration (NASA) Contract No. NASA-30627 by the applicant and D.C. Larsen and accordingly need not be described herein.

The use and operation of the invention has been described previously in detail and need not be repeated.

What is claimed is:

1. In combination with a source of visible light and a source of infra red light an endoscope that includes first and second elongate flexible elongate fiber optics that are adjacently disposed and transmit visible light from said source to an internal tissue site of a patient on which a surgical operation is to be performed and permits a surgeon to view said site when illuminated; a third elongate flexible non-toxic fiber optic adjacently disposed to said first and second fiber optics and coupled to said source of infra red light for supplying infra red light to said site to perform said surgical operation, said third fiber optic including:
   a. a core of true amorphous chalcogenide glass of a diameter greater than the wave length of said infra red light;
   b. a longitudinally extending cladding that extends around said core and is bonded thereto, said cladding having an index of refraction greater than that of said chalcogenide glass; and
   c. means for holding said first, second and third fiber optics together as an elongate flexible bundle that may be manipulated by a surgeon.

2. An invention as defined in claim 1 in which said source of infra red light is a carbon dioxide laser that emits a laser beam at 10.6 microns.

3. An invention as defined in claim 1 in which said amorphous chalcogenide glass is in the form of a drawn core that is defined by germanium, antimony and selenium.

4. An invention as defined in claim 3 in which said core is defined by germanium 25 to 35 parts by weight; antimony 5 to 15 parts by weight; and selenium 60 to 70 parts by weight.

5. An invention as defined in claim 1 in which said cladding is glass that is fused to said core.

6. An invention as defined in claim 1 in which said means is a sheath of heat shrinkable plastic that is in pressure contact with said first, second and third fiber optics.

* * * * *